United States Patent [19]

Brighton et al.

[11] Patent Number: 4,549,547

[45] Date of Patent: Oct. 29, 1985

[54] IMPLANTABLE BONE GROWTH STIMULATOR

[75] Inventors: Carl T. Brighton, Malvern; Jonathan Black, King of Prussia, both of Pa.; William Redka, Vineland, N.J.

[73] Assignee: Trustees of the University of Pennsylvania, Philadelphia, Pa.

[21] Appl. No.: 402,316

[22] Filed: Jul. 27, 1982

[51] Int. Cl.[4] ............................................. A61N 1/08
[52] U.S. Cl. ................................................. 128/419 F
[58] Field of Search ........... 128/419 R, 419 F, 419 E, 128/419 C, 908

[56] References Cited

U.S. PATENT DOCUMENTS

| | | | |
|---|---|---|---|
| 3,209,081 | 9/1965 | Ducote et al. | 179/107 |
| 3,407,363 | 10/1969 | Kaiser et al. | 331/117 |
| 3,521,087 | 7/1970 | Lombardi | 128/908 |
| 3,656,025 | 4/1972 | Roveti | 128/908 |
| 3,662,758 | 5/1972 | Glover | 128/419 E |
| 3,667,477 | 6/1972 | Susset et al. | 128/419 E |
| 3,745,995 | 7/1973 | Kraus | 128/82.1 |
| 3,783,880 | 1/1974 | Kraus | 128/82.1 |
| 3,820,534 | 6/1974 | Kraus et al. | 128/82.1 |
| 3,824,129 | 7/1974 | Fagan, Jr. | 136/6 R |
| 3,867,950 | 2/1975 | Fischell | 128/419 P |
| 3,890,953 | 6/1975 | Kraus et al. | 128/1.5 |
| 3,915,151 | 10/1975 | Kraus | 128/1.5 |
| 3,918,440 | 11/1975 | Kraus | 128/82.1 |
| 4,026,304 | 5/1977 | Levy | 128/419 F |
| 4,066,065 | 1/1978 | Kraus | 128/1.5 |
| 4,102,344 | 7/1978 | Conway et al. | 128/419 E |
| 4,105,017 | 8/1978 | Ryaby et al. | 128/1.5 |
| 4,306,564 | 12/1981 | Kraus | 128/419 F |
| 4,313,438 | 2/1982 | Greatbatch | 128/419 F |
| 4,333,469 | 6/1982 | Jeffcoat et al. | 128/419 F |
| 4,414,979 | 11/1983 | Hirshorn et al. | 128/419 F |

FOREIGN PATENT DOCUMENTS 480202  3/1975  Australia ..................... 128/419 F

OTHER PUBLICATIONS

Pisarevskii et al., "Device for Induction Electrostimulation of a Gastrointestinal Anastimosis After Gastric Resection" *Meditsinskaya Tekhnika* No. 6, Nov.-Dec. 1973, pp. 49-52.

Primary Examiner—William E. Kamm
Assistant Examiner—Mitchell J. Shein
Attorney, Agent, or Firm—Stevens, Davis, Miller & Mosher

[57] ABSTRACT

Disclosed is an implantable bone growth stimulator which needs no internal battery or large buffer capacitor. A receiving coil in a preferred embodiment, a ferrite core coil, receives RF energy from a transmitter external to the patient. The received RF energy is voltage doubled and rectified and provided to a constant current generator which in turn supplies a constant amount of current between implanted cathodes and an implanted anode. In preferred embodiments, the receiving coil, power supply, and cathodes are one unit which is located in place on an internal fixation device attached to the bones near the fracture site. In another embodiment, only the cathodes are located in the vicinity of the fracture site and the receiver coil voltage multiplier circuit and constant current source are located remote from the fracture site. Additionally, the internal fixation device in a preferred embodiment may have a plastic insert therein having one or more holes therethrough for the insertion of cathodes into the vicinity of the fracture site. While a preferred embodiment utilizes the completely implanted bone growth stimulator, the plate is effectively utilized with an external bone growth stimulator power supply and percutaneous cathodes inserted through positioning holes in the plastic insert of the fixation device.

12 Claims, 5 Drawing Figures

IMPLANTABLE BONE GROWTH STIMULATOR

BACKGROUND OF THE INVENTION

The present invention generally relates to the electronic stimulation of osteogenesis and in particular to implantable bone growth stimulators.

The electronic stimulation of bone growth (or osteogenesis) has been known for a period of time, as evidenced by U.S. Pat. No. 3,842,841, issued to Brighton, et al. on Oct. 22, 1974, entitled: "Constant Current Power Pack For Bone Healing and Method of Use". In the patent, it is disclosed that the provision of a cathode inserted at or near a bone fracture site and connected to a Direct Current source with an anode taped to the patient's skin will stimulate bone growth at the fracture site. A publication by Zimmer.USA, Inc., literature No. B-2360-1, revised in September, 1979, available from Zimmer.USA, 727 North Detroit Street, Post Office Box 708, Warsaw, Ind. 46580, provides a detailed description of Direct Current bone growth stimulation and one advantageous system to implement such stimulation. In such a system, the bone growth stimulating current and/or the cathode is inserted transcutaneously into the region of the fracture site. This insertion of a foreign object through the skin provides a possible point for infection of the skin and fracture site.

Thus, it is desirable to be able to totally implant a bone growth stimulation device. Many heart pacemakers are implanted and powered by an external current supply. Of course, the current level required to operate a heart pacemaker is an order of magnitude less than that current required for bone growth stimulation. Further, while the pacemaker can effectively utilize Alternating Current, the bone growth stimulation process, as embodied in the referenced patent, requires Direct Current.

These conditions have been met in the past through the utilization of a battery powered implantable bone growth stimulator, wherein the battery pack, power supply, and associated connections are totally implanted under the patient's skin, allowing the skin to heal thereover, preventing the possibility of infection. Unfortunately, a battery has a limited life and many patient's after the limb has healed to a certain extent, do not complete follow-up visits to their doctor to permit the doctor to remove the bone growth stimulator. Consequently, the battery pack may remain implanted for many years. Eventually, other problems can be created by the decomposition and/or deterioration of the battery pack, which may require extensive surgery at some point in the future. The elimination of the battery has been considered by researchers in the bone growth stimulation area as a positive improvement. However, it was conventionally thought that it would be necessary to have at least a buffer battery, or a large buffer capacitor of some sort, to provide a needed reference voltage for the constant current generator which powered the cathodes located in the fracture site.

SUMMARY OF THE INVENTION

In accordance with the prior art difficulties, it is an object of the present invention to provide an implantable, completely self-contained bone growth stimulator.

It is a further object of the present invention to provide an implantable bone growth stimulator which does not require the implantation of a battery under the patient's skin surface.

It is an additional object of the present invention to provide an implantable bone growth stimulator which does not require either a buffer battery or a buffer capacitor to be implanted under the patient's skin surface.

It is a still further object of the present invention to provide an implantable bone growth stimulator which can provide relatively high current levels for a D.C., constant current, source.

It is a still further object of the present invention to provide an implantable bone growth stimulator in combination with an implantable cathode and anode which are sized so as to enhance bone growth stimulation without causing tissue necrosis.

It is a further object of the present invention to provide an implantable fixation device for cooperation with an external power supply where the fixation device serves to locate the cathode of an osteogenesis stimulation device.

It is a still further object to provide an implantable bone growth stimulator having a remote cathode which can be used in conjunction with or apart from an internal fixation device.

It is an additional object of the present invention to provide an implantable bone growth stimulator which includes a fixation plane which can be utilized to fix the position of bones in the vicinity of a fracture site.

The above and other objects are achieved in accordance with the present invention by providing a transmitting coil external to the patient's skin which is supplied by a radio frequency power source. Electromagnetic radiation is transmitted through the skin and received by a coil contained in the implantable bone growth stimulator. The coil's output is voltage multiplied and rectified and supplied to a conventional implanted constant current power supply. The constant current power supply outputs are connected to the bone growth stimulating cathode located in the vicinity of the fracture site and an anode on one surface of the implantable bone growth stimulator.

DETAILED DESCRIPTION OF PREFERRED EMBODIMENTS

Figure 1:
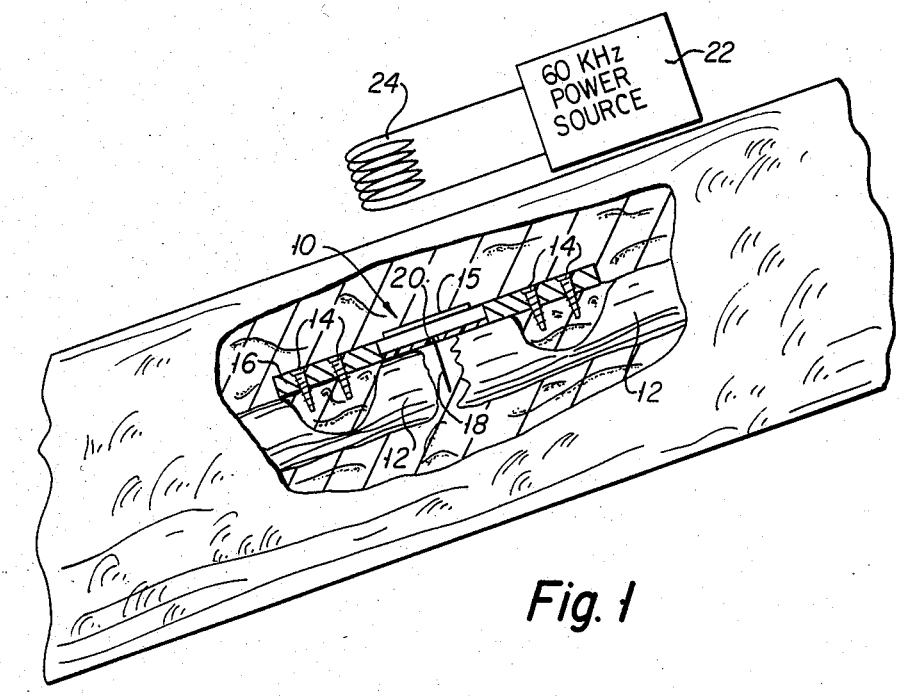
FIG. 1 is a side view, partially in section, of the implantable bone growth stimulating device in position at a fracture site.

Referring now more particularly to the Drawings, wherein like reference numerals indicate identical elements in the several views, FIG. 1 illustrates the implantable bone growth stimulator 10 which is attached to a metallic fixation device 16 which in turn is attached to bones 12 by means of screws 14. The implantable bone growth stimulator comprises the anode plate 15, the cathode 18, and the electronic power supply 20.

An external power supply 22 is connected to a transmitting coil 24, which radiates electromagnetic energy through the skin 12 to the vicinity of the implantable bone growth stimulator 10. In preferred embodiments, the power supply operates at a frequency of 60 KHz, although other frequencies may be more advantageous (the higher the frequency, the smaller the receiver coil which is located in the electronic power supply implanted under the patient's skin). In this preferred embodiment, it can be seen that plate 16 serves not only to mount the electronic power supply 20, but also positions bone 12 which has been fractured.

Figure 2:
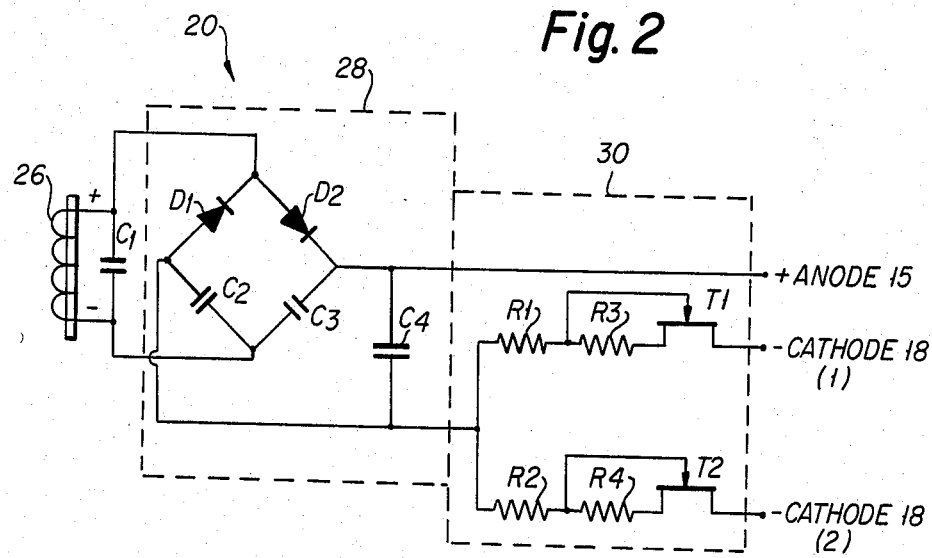
FIG. 2 is a partial circuit diagram illustrating the electronic circuitry contained on the implantable bone growth stimulator.

FIG. 2 illustrates one embodiment of the electronic power supply 20, and it should be noted that, as illustrated, capacitors C1 and C4 are 5000 pF and C2 and C3 are 10,000 pF. The diodes disclosed are zero bias Schottky diodes and transisters T1 and T2 are 2N4338. Resistors R1 and R2 are 1K ohm and R3 and R4 are 33K ohm resistors. Other suitable capacitors, diodes, transistors and resistors could be utilized and would be obvious to one of ordinary skill in the art in view of this disclosure. The radio frequency electromagnetic radiation from transmitting coil 24 is received by receiver coil 26 in which the actual number of turns is determined by the magnitude of signal desired and the physical size limitations of the coil. The arrangement of diodes and capacitors as shown are a conventional full wave voltage doubler which serves to rectify the output of coil 26 while at the same time multiplies the voltage level by a factor of 2. Therefore, the output voltage (D.C. out) from the voltage multiplier circuit will be a rectified voltage equal to two times the output voltage of coil 26 which is identified as $E_{IN}$. The output of the voltage multiplier circuit is supplied to a constant current source 30 which has a negative and positive output which are connected to the cathodes 18 and the anode plate 15, respectively. Obviously, if more or less cathodes are desired, there could be just one, or three or more cathode supply circuits. The constant current source may be an implantable version of the external constant current source disclosed in the previously discussed Zimmer.USA publication, or may be any other source capable of providing approximately 20 milliamps of current from each port on the cathode.

It has been found advantageous to use a cathode which is covered with insulation, except for very small exposed areas (called ports). The discussion of port sizes, distributions, and current densities is not the subject of the present invention and would be obvious to those of ordinary skill in the art in view of an article entitled "Electrically Induced Osteogenesis: Relationship Between Charge, Current Density, and the Amount of Bone Formed", which appeared in *Clinical Orthopedics*, Vol. 161, published in November, 1981. However, where it is desirable to utilize a multi-port cathode, the constant current source 30 supplies an amount of current to the cathode (or cathodes) equal to the optimum current level per port times the number of ports.

Figure 3:
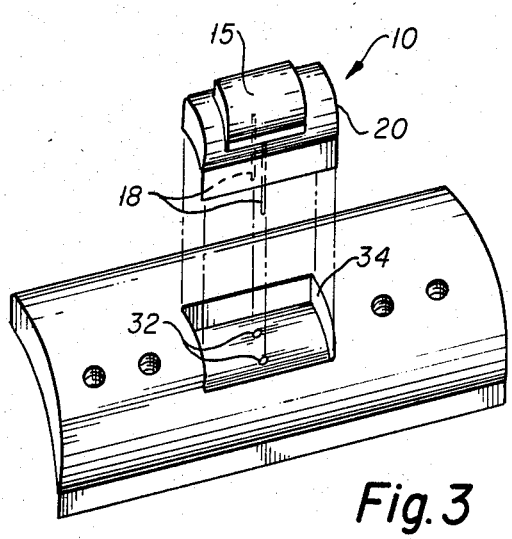
FIG. 3 is a perspective view illustrating a further embodiment of the implantable bone growth stimulator.

Although FIG. 1 illustrates the electronic power supply formed integrally with the fixation plate, it may be desirable to have a variety of fixation plates and a variety of electronic power supplies which can be combined depending upon the specific medical requirements of the patient. This is believed within the spirit of the present invention and is illustrated in FIG. 3, wherein the electronic power supply 20 is a separate structure from the fixation plate 16. To prevent shorting of current from the multiple cathodes 18, the electronic power supply 20 is mounted such that the cathodes extend through holes 32 in a plastic insulating plug 34. Clearly, the fixation plate equipped with the insulating plug (extending therethrough) could be manufactured perhaps without any cathode mounting holes 32 located therein. During the fixation plate implantation process, the patient's surgeon would make a determination as to whether a single or multiple cathode electronic power supply would be needed and then drill the appropriate holes in the plastic plug. Obviously, the constant current source 30 which would be contained in the electronic power supply 20 would be sized to meet the current needs determined by the number of cathodes mounted with the electronic power supply 20.

Figure 4:
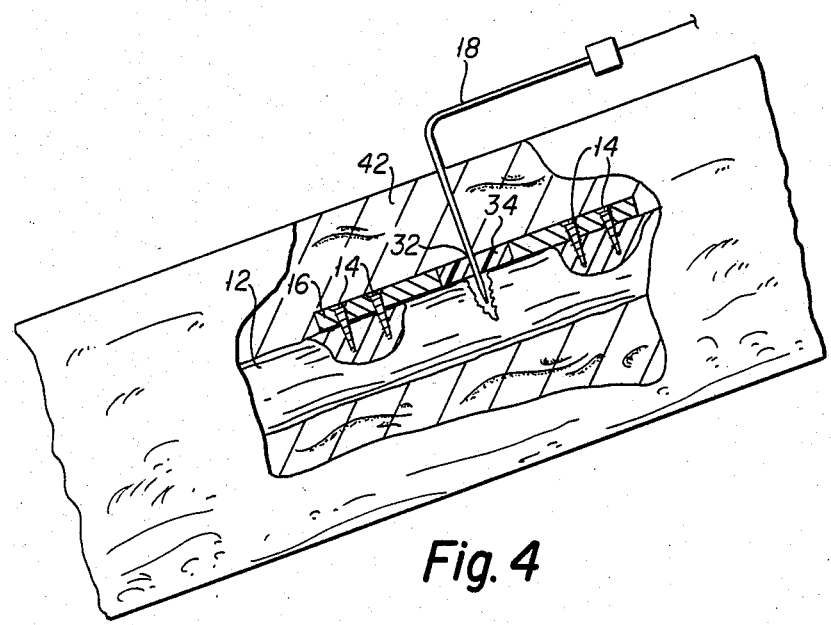
FIG. 4 is a side view, partially in section, of the implanted fixation plate in conjunction with externally powered cathodes.

Although it is preferred to implant the complete power supply and receiver system, it may be desirable to utilize just the concept of the fixation plate to mount and position the cathodes and thus the embodiment shown in FIG. 4 is encompassed within the scope of the present invention. Here, fixation plate 16 is fixed on bone 12 which has a stress fracture 40. Cathode 18 is inserted through the patient's skin and muscle tissue 42, through mounting hole 32 in the plastic plug into the fracture site 40. It is envisioned that a conventional surgical wrapping and/or cast would be used in conjunction with this fixation plate. However, it is important to note that the primary fixation and location of the cathode 18 is by means of its insertion through the plastic insulating plug of the fixation plate.

Figure 5:
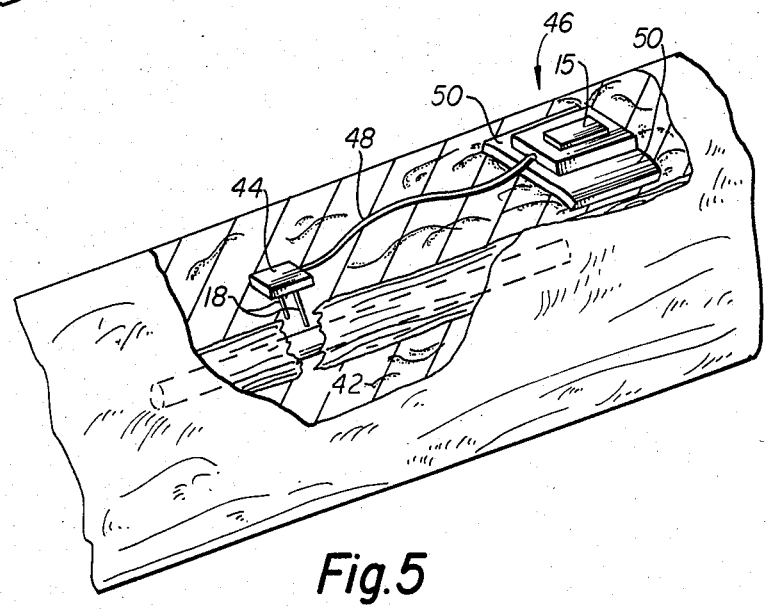
FIG. 5 is a side view of a further embodiment of the invention having multiple cathodes remote from the power supply and anode.

FIG. 5 illustrates another version of the present invention in which bone 12 is fractured and contains a different fixation device; for example, in intramedullary rod 42. A cathode support button 44 holds the cathodes in their proper alignment and serves to electrically connect the cathodes to the power supply; in this instance, remote power supply 46. In the event the location of the power supply in the vicinity of the fracture site (as indicated in FIGS. 1 and 3) is undesirable, a remote power supply 46 can be used and located at a point away from the fracture site where it may more easily be implanted in the muscle and tissue mass. The same or similar electronic circuitry would be used and the one or more cathodes (FIG. 5 illustrates two cathodes 18) would be independently connected to the power supply through an insulated connecting cord 48. It is advantageous to equip the power supply which is not attached or supported by the fixation plate (such as remote power supply 46) with perforated or surface treated tabs 50 which provide a surface on or through which cell tissues can adhere, fixing the device at its implanted location. Such a tab material may be a porous polysulfone or other materials known for such purposes. It is clear that while the power supply 20 and the remote power supply 46 are shown at least operating in conjunction with an internal fixation device, that they could operate with a conventional external fixation device (e.g., a cast) or without any fixation device at all (perhaps in the case of a minor stress fracture, bone chip, etc.).

In accordance with the above disclosure, many embodiments, improvements and modifications of the present invention will be obvious to those of ordinary skill in the art. It is clear that the fixation plate, the cathodes, and the electronic power supply would all be comprised, or at least coated, with a bio-compatible material to prevent detrimental rejection reactions by local skin tissue in the area of implantation. The term "bio-compatible material" for the purposes of this specification and claims, means a material which shows acceptable, acute and chronic local tissue response and could be Teflon ®, silicone, ceramics, etc. Any external power supply could be used to provide relatively high frequency energy to the transmitting coil 24. This transmitting coil could be located on the skin adjacent the implantable bone growth stimulator, or could surround the limb to which the implantable bone growth stimulator is affixed, or could be located some distance away. In a preferred embodiment a receiver coil and sensing circuit is also provided to sense the 120 KHz signal broadcast by the implanted bone growth stimulater as an indication of a anode-cathode circuit continuity. The external source of the power supply could be standard line voltage of 115 volts, or, in a preferred embodiment, could be a battery pack which permits the external power supply 22 and transmitting coil 24 to be worn by the patient during those periods of time when electrical stimulation of osteogenesis is desired.

Thus, in view of the above teachings, modifications of the electronic circuits and the apparatus interrelationships will be obvious to those of ordinary skill in the art. Therefore, the present invention is not limited to the embodiments and applications expressed herein, and is only limited in accordance with the appended claims.

We claim:

1. An implantable bone growth stimulator, powered by electromagnetic radiation external to a patient, said stimulator comprising:
   at least one cathode;
   at least one anode;
   means for receiving electromagnetic radiation;
   means, responsive to said receiving means, for rectifying said received electromagnetic radiation, said rectifying means including an output; and
   means, responsive to said rectifying means output and connected to said at least one cathode and to said at least one anode, for maintaining at a desired substantially constant level one of voltage and current supplied between said at least one cathode and said at least one anode.

2. An implantable bone growth stimulator according to claim 1, wherein said receiving means comprises a coil of wire wound around a core.

3. An implantable bone growth stimulator according to claim 2, wherein said rectifying means comprises a full wave voltage doubler having a positive and negative output.

4. An implantable bone growth stimulator according to claim 3, wherein said controlling means comprises a constant current source.

5. An implantable bone growth stimulator according to claim 4, wherein said constant current source comprises:
   a junction field effect transistor; and
   an at least two resistor voltage divider, where the voltage divider and source/drain of the transistor are connected in series between said at least one cathode and said negative output of said voltage doubler, with said transistor gate being connected to a junction between said at least two resistors.

6. An implantable bone growth stimulator according to one of claims 1 through 5, wherein said at least one cathode is remote from said receiving means, said rectifying means, said controlling means, and said at least one anode.

7. An implantable bone growth stimulator according to claim 6, wherein said stimulator further includes a cathode positioning device for positioning at least one cathode in a region of desired bone growth, said device comprising:
   means, attachable to a bone whose growth is to be stimulated, for mechanically strengthening said bone in said region of desired bone growth;
   means for attaching said strengthening means to said bone;
   insulation means, located in said strengthening means and in the vicinity of said region of desired bone growth, for insulating said at least one cathode from said strengthening means; and
   means for defining at least one hole through said insulating means and for receiving said at least one cathode in conjunction with bone growth stimulation and for positioning said at least one cathode in the vicinity of said desired bone growth stimulation.

8. An implantable bone growth stimulator according to claim 7, wherein said strengthening means comprises a surgical steel fixation plate, said insulating means comprises a plastic insert in said plate, said attaching means comprises screws, and said defining and positioning means comprises at least one hole through said insulation means.

9. An implantable bone growth stimulator according to claim 7, wherein said receiving means, said rectifying means, said controlling means, and said at least one anode are an integral unit, said stimulator including tab means for positioning said unit in tissue remote from said region of desired bone growth.

10. An implantable bone growth stimulator according to one of claims 1 through 5, wherein said receiving means, said rectifying means, said controlling means, said at least one anode, and said at least one cathode are an integral unit, said at least one anode comprising a surface portion of said unit and said at least one cathode protruding from said unit into a region of desired bone growth.

11. An implantable bone growth stimulator according to claim 10, wherein said stimulator further includes a cathode positioning device for positioning said at least one cathode in said region of desired bone growth, said device comprising:
   means, attachable to a bone whose growth is to be stimulated, for mechanically strengthening said bone in said region of desired bone growth;
   means for attaching said strengthening means to said bone;
   insulation means, located in said mechanical strengthening means and in the vicinity of said region of desired bone growth, for insulating said at least one cathode from said mechanical strengthening means; and
   means for defining at least one hole through said insulating means and for receiving said at least one cathode in conjunction with bone growth stimulation and for positioning said at least one cathode in the vicinity of said desired bone growth stimulation.

12. An implantable bone growth stimulator according to claim 11, wherein said at least one cathode comprises means for attaching said unit to said positioning device.

* * * * *